United States Patent [19]
Schnepf et al.

[11] Patent Number: 5,508,032
[45] Date of Patent: Apr. 16, 1996

[54] BACILLUS THURINGIENSIS ISOLATES ACTIVE AGAINST COCKROACHES

[75] Inventors: H. Ernest Schnepf, San Diego, Calif.; John B. Randall, Racine, Wis.; Jewel M. Payne, Davis, Calif.

[73] Assignee: Mycogen Corporation, San Diego, Calif.

[21] Appl. No.: 269,421

[22] Filed: Jun. 30, 1994

[51] Int. Cl.$^6$ .............................. A01N 63/04; C12N 1/20
[52] U.S. Cl. ..................... 424/93.462; 424/84; 514/2
[58] Field of Search ............................... 424/93.462, 84; 514/2

[56] References Cited

U.S. PATENT DOCUMENTS

| | | | |
|---|---|---|---|
| 4,448,885 | 5/1984 | Schnepf et al. | 435/252.33 |
| 4,467,036 | 8/1984 | Schnepf et al. | 475/320.1 |
| 4,797,276 | 1/1989 | Herrnstadt et al. | 424/84 |
| 4,849,217 | 7/1989 | Soares et al. | 424/84 |
| 4,853,331 | 8/1989 | Herrnstadt et al. | 435/252.1 |
| 4,918,006 | 4/1990 | Ellar et al. | 435/69.1 |
| 4,948,734 | 8/1990 | Edwards et al. | 514/2 |
| 5,151,363 | 9/1992 | Payne | 435/252.5 |
| 5,298,245 | 3/1994 | Payne et al. | 424/93.462 |
| 5,302,387 | 4/1994 | Payne et al. | 424/93.462 |

FOREIGN PATENT DOCUMENTS 0409438  1/1991  European Pat. Off. .

OTHER PUBLICATIONS

Beegle, C. C. (1978) "Use of Entomogenous Bacteria in Agroecosystems" Developments in Industrial Microbiology 20:97–104.

Couch, T. L. (1980) "Mosquito Pathogenicity of *Bacillus thuringiensis var. isrealensis*" Developments in Industrial Microbiology 22:61–76.

Feitelson, Jerald S. et al., (1992) "*Bacillus thuringiensis*: Insects and Beyond" Bio/Technology 10:271–275.

Gaertner, Frank (1990) "Cellular delivery systems for insecticidal proteins: living and non-living microorganisms" Controlled Delivery of Crop-Protection Agents, pp. 245–255.

Gaertner, F., L. Kim (1988) "Current Applied Recombinant DNA Projects" TIBTECH 6:S4–S7.

Hofte, H., H. R. Whiteley (1989) "Insecticidal Crystal Proteins of *Bacillus thuringiensis*" Microbiological Reviews 53(2):242–255.

Krieg, Von A. et al., (1983) "Bacillus thuringiensis var. tenebrionis: ein neuer, gegenuber Larven von Coleopteren wirksamer Pathotyp" Z. ang. Ent. 96:500–508.

Jaquet, Francoise et al. (1987) "Specificity of *Bacillus thuringiensis* Delta–Endotoxin" Applied and Environmental microbiology 53(3):500–504.

Singh, Gur Jai Pal, Sarjeet S. Gill (1985) "Myotoxic and Neurotoxic Activity of *Bacillus thuringiensis* var. *israelensis* Crystal Toxin" Pesticide Biochemistry and Physiology 24:406–414.

Lambert, Bart et al. (1992) "Novel *Bacillus thuringiensis* Insecticidal Crystal Protein with a Silent Activity against Coleopteran Larvae" Applied and Environmental Microbiology 58(8):2536–2542.

Primary Examiner—Mindy Fleishep
Assistant Examiner—David Schmickel
Attorney, Agent, or Firm—Saliwanchik & Saliwanchik

[57] ABSTRACT

The subject invention concerns novel materials and methods for the control of cockroaches. Cockroaches are common house pests, and they create problems in hospitals, the food industry and in agriculture. According to the subject invention, activated toxins of *Bacillus thuringiensis* var. israelensis (*B.t.i.*) are used to control cockroaches. In one embodiment, the subject invention also concerns the use of *B.t.* PS123D1 to control cockroaches. A truncated form of a toxin obtained from PS123D1 having particular activity to cockroaches is also claimed for use in controlling the pest.

9 Claims, 1 Drawing Sheet

Figure 1

BACILLUS THURINGIENSIS ISOLATES ACTIVE AGAINST COCKROACHES

BACKGROUND OF THE INVENTION

The soil microbe *Bacillus thuringiensis* (*B.t.*) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain *B.t.* toxin genes have been isolated and sequenced, and recombinant DNA-based *B.t.* products have been produced and approved for use. In addition, with the use of genetic engineering techniques, new approaches for delivering *B.t.* endotoxins to agricultural environments are under development, including the use of plants genetically engineered with endotoxin genes for insect resistance and the use of stabilized intact microbial cells as *B.t.* endotoxin delivery vehicles (Gaertner and Kim, 1988). Thus, isolated *B.t.* endotoxin genes are becoming commercially valuable.

Until the last ten years, commercial use of *B.t.* pesticides has been largely restricted to a narrow range of lepidopteran (caterpillar) pests. Preparations of the spores and crystals of *B. thuringiensis* var. kurstaki have been used for many years as commercial insecticides for lepidopteran pests. For example, *B. thudngiensis* var. kurstaki HD-1 produces a crystal called a delta endotoxin which is toxic to the larvae of a number of lepidopteran insects.

In recent years, however, investigators have discovered *B.t.* pesticides with specificities for a much broader range of pests. For example, other species of *B.t.*, namely *B.t.* var. israelends and *B.t.* var. tenebdonis (a.k.a. M-7, a.k.a.*B.t.* var. san diego), have been used commercially to control insects of the orders Diptera and Coleoptera, respectively (Gaertner, 1989). See also Couch, 1980 and Beegle, 1978. Krieget al, 1983, describe *Bacillus thuringiensis* var. tenebrionis, which is reportedly active against two beetles in the order Coleoptera. These are the Colorado potato beetle, *Leptinotarsa decemlineata*, and the beetle *Agelastica alni*.

Recently, new subspecies of *B.t.* have been identified, and genes responsible for active δ-endotoxin proteins have been isolated (Höfte and Whitelcy, 1989). Höfte and Whiteley classified *B.t.* crystal protein genes into 4 major classes. The classes were CryI (Lepidoptera-specific), CryII (Lepidoptera- and Diptera-specific), CryIII (Coleoptera-specific), and CryIV (Diptera-specific). Prefontaine et al., 1987, describe probes useful in classifying lepidopteran-active genes. The discovery of strains specifically toxic to other pests has been reported (Feitelson et al., 1992).

*B.t.* crystalline toxins are generally recognized as being protoms, requiring either particular physicochemical conditions (i.e., pH, redox, ionic strength), or the action of certain proteases, or both, to generate an active toxin (Höfte and Whitelcy, 1989). In most cases, the insect supplies conditions for activation of the toxin; however, cases have been documented where pre-solubilization or pre-proteolysis have been necessary for optimum activity (Jacquet et al., 1987) or detection of activity (Höfte et al., 1992).

The cloning and expression of a *B.t.* crystal protein gene in *Escherichia coli* has been described in the published literature (Schnepf and Whiteley, 1981). U.S. Pat. No. 4,448,885 and U.S. Pat. No. 4,467,036 both disclose the expression of *B.t.* crystal proteins in *E. coli*. U.S. Pat. Nos. 4,797,276 and 4,853,331 disclose *B. thuringiensis* var. tenebrionis (a.k.a.*B.t.* san diego, a.k.a. M-7) which can be used to control coleopteran pests in various environments. U.S. Pat. No. 4,918,006 discloses *Bacillus thuringiensis* var. israelensis toxins which are active against dipteran pests. This patent reports that a protein of about 27 kD, and fragments thereof, are responsible for the dipteran activity. U.S. Pat. No. 4,849,217 discloses *B.t.* isolates which have activity against the alfalfa weevil. U.S. Pat. No. 5,151,363 and U.S. Pat. No. 4,948,734 disclose certain isolates of *B.t.* which have activity against nematodes. As a result of extensive research and investment of resources, other patents have issued for new *B.t.* isolates and new uses of *B.t.* isolates. However, the discovery of new *B.t.* isolates and new uses of known *B.t.* isolates remains an empirical, unpredictable art.

Cockroaches such as the German cockroach (*Blatella germanica*), Oriental cockroach (*Blatta orientalis*), American cockroach (*Periplaneta americana*) and Brown cockroach (*Periplaneta americana*) are some of the most important insect pests to infest homes and commercial structures. These pests have omnivorous feeding habits resulting in the destruction of food, leather and fabrics. Cockroaches have also been implicated in the transmission of the disease-causing organisms Salmonella and Toxoplasma. Additionally, cockroaches contain altergins, to which approximately 7.5 percent of the human population are sensitive.

Although *B.t.* toxicity to cockroaches has been reported (Singh and Gill, 1985), this toxicity could only be achieved by directly injecting solubilized *B.t.* crystals into the foregut or hemocoel of the cockroaches. Attempts to feed or force-feed *B.t.* preparations to the cockroaches were unsuccessful.

Cockroaches are frequently controlled with insecticidal baits. Because these baits are used in homes and restaurants, cockroach insecticides must be safe to humans. The heavy use of synthetic insecticides has resulted in the selection of resistant cockroach populations. New insecticides, safe for use around humans, are necessary to control these resistant populations.

BRIEF SUMMARY OF THE INVENTION

The subject invention concerns the discovery and use of cockroach-active *Bacillus thuringiensis* (*B.t.*) cultures which produce cockroach-active protein toxins. The materials and methods set forth herein pertain particularly to *Bacillus thuringiensis* var. israelensis. Specifically exemplified herein is the use of the *B.t.* isolate known as PS123D1. The subject invention also includes the use of variants of the exemplified *B.t.* isolate which have substantially the same pesticidal properties as the exemplified isolate. These variants would include routants. Procedures for making mutants are well known in the microbiological art. Ultraviolet light and nitrosoguanidine are used extensively toward this end.

According to the subject invention, cockroaches may be controlled using the PS123D1 isolate itself (or other *B.t.*i. isolate), variants of PS123D1, toxins obtained from said isolates, commercial preparations made from cultures of these isolates, or toxins produced by DNA of these isolates, wherein said DNA has been transformed into another host. Further, the invention also includes the treatment of substantially intact cells of either a *B.t.* isolate or recombinant cells containing DNA from an isolate, to prolong the pesticidal activity when the substantially intact cells are applied to the environment of a target pest.

The activity described herein is attributable to the approximately 28 to 33 kD toxin of a *B.t.*i. isolate or, preferably, to modified forms of this toxin. In a preferred embodiment of the subject invention, truncated forms of the 28 kDa PS123D1 toxin have been found to be particularly active against cockroaches. A specific example is the truncated toxin which has amino acids removed from the N-terminus and is about 25 kDa. As described herein, the highly active truncated forms of the toxins of the subject invention can be surprisingly obtained through treatment of B.t. culture supernatants and/or by growing B.t. cultures under appropriate conditions to result in the production of active toxins as a result of the advantageous effects of endogenous proteases. Other modifications which cause, for example, solubilization of the B.t.i. toxin can also be utilized to obtain highly active cockroach toxins.

DETAILED DISCLOSURE OF THE INVENTION

The subject invention concerns the discovery of *Bacillus thudngiensis* (*B.t.*) cultures and toxins with excellent activity against cockroaches and other orthopterans. As used herein, "orthopterans" include, for example, Orthoptera and Dictyoptera. In a preferred embodiment of the subject invention, the *B.t.* cultures utilized are *B.t.* var. israelensis. The israelensis variety is well known and readily recognized by those skilled in this art. Characteristics generally associated with the israelensis category of *B.t.* include dipteran activity, H14 serotype, and a protein pattern which includes an approximately 28 to 33 kD protein and, generally, additional proteins of about 70 kD and 130 kD. Other *B.t.* varieties which express israelensis-type toxins can also be used according to the subject invention. Such toxins would have a size similar to the toxins produced by *B.t.i.* and a similar activity profile, including dipteran activity. *B.t.* var. morrisoni serotype 8a,8b have, for example, been reported to express *B.t.i.*-type toms. An example of such an isolate is PS71M3. As used herein, the term "*Bacillus thuringiensis* var. israelensis toxin" includes toxins which are similar or related to toxins expressed by *B.t.i.* but which happen to be expressed by a different variety of *B.t.*

Specifically exemplified herein is a toxin obtainable from the *B.t.* isolate designated PS123D1. In a preferred embodiment of the subject invention, the approximately 28 kDa toxin expressed by PS123D1 is truncated to yield a toxin of approximately 25 kDa having high biological activity against cockroaches. This truncated toxin preferably has amino acids removed from the N-terminus to yield the active truncated forms. As described herein, the removal of amino acids to yield the truncated active form can be accomplished using a variety of techniques which include treatment of the *B.t.* cultures and growing the cultures under appropriate conditions such that endogenous proteases cleave the protein to its highly active form.

Although the truncated toxin has been found to have unexpected toxicity against orthopterans, direct production of this truncated toxin using a truncated gene is not the preferred embodiment of the subject invention. Expression of the truncated toxin has been found to result in poor expression and/or significant toxicity to *E. coli* and Pseudomonas host cells. Surprisingly, however, it has been discovered that full length *B.t.i.* toxins of about 28–33 kDa can be expressed then convened to highly active forms through addition of appropriate reagents and/or by growing the cultures under conditions which result in the truncation of the proteins through the fortuitous action of endogenous proteases.

In an alternative embodiment, the full length toxin may undergo other modification to yield the active form of the toxin. This other modification could include, for example, solubilization of the full length toxin. Adjustment of pH, ionic strength, or redox potential can be used to effect the desired modification of the full length toxin to yield an active form.

The *Bacillus thuringiensis* isolate PS123D1 has the following characteristics in its biologically pure form:

TABLE 1

| Characteristics of B.t. PS123D1 | |
|---|---|
| | B.t. PS123D1 |
| Inclusions: | amorphic |
| Approximate molecular wt. of proteins by SDS-PAGE | 133,000 |
| | 127,000 |
| | 72,000 |
| | 28,000 |
| Host range | Cockroaches |
| | Diptera |

The cultures disclosed in this application have been deposited in the Agricultural Research Service Patent Culture Collection (NRRL), Northern Regional Research Center, 1815 North University Street, Peoria, Ill. 61604, USA.

| Culture | Repository No. | Deposit date |
|---|---|---|
| *Bacillus thuringiensis* PS123D1 | NRRL B-21011 | October 13, 1992 |
| *Bacillus thuringiensis* PS71M3 | NRRL B-18930 | December 27, 1991 |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposit(s) should the depository be unable to furnish a sample when requested, due to the condition of the deposit(s). All restrictions on the availability to the public of the subject culture deposits will be irrevocably removed upon the granting of a patent disclosing them.

Genes and toxins. The genes and toxins useful according to the subject invention include not only the full length sequences disclosed but also fragments of these sequences, variants, mutants, and fusion proteins which retain the characteristic pesticidal activity of the toxins specifically exemplified. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins.

It should be apparent to a person skilled in this art that genes encoding cockroach-active toxins can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toms.

Equivalent toxins and/or genes encoding these equivalent toxins can be derived from *B.t.* isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other *B.t.* toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toxins, can readily be prepared using standard procedures in this art. The genes which encode these toxins can then be obtained from the microorganism.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity.

A further method for identifying the toxins and genes of the subject invention is through the use of oligonucleotide probes. These probes are nucleotide sequences having a means for detection. As is well known in the art, if the probe molecule and nucleic acid sample hybridize by forming a strong bond between the two molecules, it can be reasonably assumed that the probe and sample have substantial homology. The probe's means of detection provides a means for determining in a known manner whether hybridization has occurred. Such a probe analysis provides a rapid method for identifying toxin-encoding genes of the subject invention. The nucleotide segments which are used as probes according to the invention can be synthesized by use of DNA synthesizers using standard procedures. These nucleotide sequences can also be used as PCR primers to amplify genes of the subject invention.

Certain toxins of the subject invention have been specifically exemplified herein. Since these toxins are merely exemplary of the toxins of the subject invention, it should be readily apparent that the subject invention further comprises variant or equivalent toxins (and nucleotide sequences coding for equivalent toxins) having the same or essentially the same pesticidal activity of the exemplified toxins. These equivalent toxins can have amino acid homology with an exemplified toxin. This amino acid homology will typically be greater than 75%, preferably be greater than 90%, and most preferably be greater than 95%. The amino acid homology will be highest in certain critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 2 provides a listing of examples of amino acids belonging to each class.

TABLE 2

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The toxins of the subject invention can also be characterized in terms of the shape and location of toxin inclusions, which are described above.

Recombinant hosts. The toxin-encoding genes harbored by the isolates of the subject invention can be introduced into a wide variety of microbial or plant hosts. Expression of the toxin gene results, directly or indirectly, in the intracellular production and maintenance of the pesticide. With suitable microbial hosts, e.g., Pseudomonas, the microbes can be applied to the situs of the pest, where they will proliferate and be ingested by the pest. The result is a control of the pest. Alternatively, the microbe hosting the toxin gene can be treated under conditions that prolong the activity of the toxin and stabilize the cell. The treated cell, which retains the toxic activity, then can be applied to the environment of the target pest.

Where the *B.t.* toxin gene is introduced via a suitable vector into a microbial host, and said host is applied to the environment in a living state, it is advantageous to use certain host microbes. For example, microorganism hosts can be selected which are known to occupy the pest's habitat. Microorganism hosts may also live symbiotically with a specific species of cockroach. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the habitat of the cockroach. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, e.g., genera Metarhizium, Bavaria, Saccharomyces, Cryptococcus, Kluyveromyces, Sporobolomyces, Rhodotorula, and Aureobasidium. Of particular interest are such bacterial species as *Pseudomonas syringae, Pseudomonas fluorescens, Serratia marcescens, Acetobacter xylinum, Agobacterium tumefaciens, Rhodopseudomonas spheroides, Xanthomonas campestris, Rhizobium melioti, Alcaligenes entrophus,* and *Azotobacter vinlandii*; and yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans*. Of particular interest are the pigmented microorganisms.

A wide variety of ways are available for introducing a *B.t.* gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Treatment of cells. As mentioned above, *B.t.* or recombinant cells expressing a *B.t.* toxin can be treated to prolong the toxin activity and stabilize the cell. The pesticide microcapsule that is formed comprises the *B.t.* toxin within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids, and Hetty's fixative (See: Humason, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of cell treatment retains at least a substantial portion of the bio-availability or bioactivity of the toxin.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells of the invention can be cultured using standard art media and fermentation techniques. Upon completion of the fermentation cycle the bacteria can be harvested by first separating the *B.t.* spores and crystals from the fermentation broth by means well known in the art. The recovered *B.t.* spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations. Formulated bait granules containing an attractant and spores and crystals of the *B.t.* isolates, or recombinant microbes comprising the genes obtainable from the *B.t.* isolates disclosed herein, can be applied to the environment of the cockroach. The bait may be applied liberally since the toxin does not affect animals or humans. Product may also be formulated as a spray or powder. Cockroaches pick the product up on their feet or abdomen and carry it back to the nest where other cockroaches will be exposed to the to, tin. The *B.t.* isolate or recombinant host expressing the *B.t.* gene may also be incorporated into a bait or food source for the cockroach.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the cockroaches, e.g., baseboards, walls, floors, by spraying, dusting, sprinkling, baiting, or the like.

Mutants. Mutants of the novel isolates of the invention can be made by procedures well known in the art. For example, an asporogenous mutant can be obtained through ethylmethane sulfonate (EMS) mutagenesis of a novel isolate. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell treatment process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. Isolates

A subculture of the B.t. isolate can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4 \cdot 7H_2O$ | 2.46 g |
| $MnSO_4 \cdot H_2O$ | 0.04 g |
| $ZnSO_4 \cdot 7H_2O$ | 0.28 g |
| $FeSO_4 \cdot 7H_2O$ | 0.40 g |
| $CaCl_2$ Solution (100 ml) | |
| $CaCl_2 \cdot 2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and crystals, obtained in the above fermentation, can be isolated by procedures well known in the art. A frequently-used procedure is to subject the harvested fermentation broth to separation techniques, e.g., centrifugation.

EXAMPLE 2

Purification and Amino Acid Sequencing

A *Bacillus thuringiensis* (B.t.) can be cultured as described in Example 1 or by using other standard media and fermentation techniques well known in the art. Delta-endotoxin can be isolated and purified by harvesting toxin protein inclusions by standard sedimentation centrifugation. The recovered protein inclusions can be partially purified by sodium bromide (28–38%) isopycnic gradient centrifugation (Pfannenstiel et al, 1984). Thereafter the individual toxin proteins can be resolved by solubilizing the crystalline protein complex in an alkali buffer and fractionating the individual proteins by DEAE-sepharose CL-6B (Sigma Chem. Co., St. Louis, Mo.) chromatography by step-wise increments of increasing concentrations of an NaCl-containing buffer (Reichenberg, 1957).

EXAMPLE 3

Testing of B.t. Isolate PS123D1

The spore-crystal pellet of B.t. strain PS123D1 was suspended in 0.1M $Na_2CO_3$ buffer, pH 11, containing 0.5% β-mercaptoethanol (ME) which disrupts disulfide bands. The procedure utilized concentrated the cells (and toxin) by about 30% compared to the concentration achieved at the end of the culture techniques as described in Example 1. The suspension was left at room temperature for 1 hour. The pH is then lowered and the ME removed by dialysis against 15 volumes of 0.1M $Na_2CO_3$ buffer, pH 9.5 at room temperature for 3 hours (Treatment I). In a second treatment (Treatment II), the dialysis buffer was used in the initial incubation, thereby maintaining a lower pH.

Figure 1:
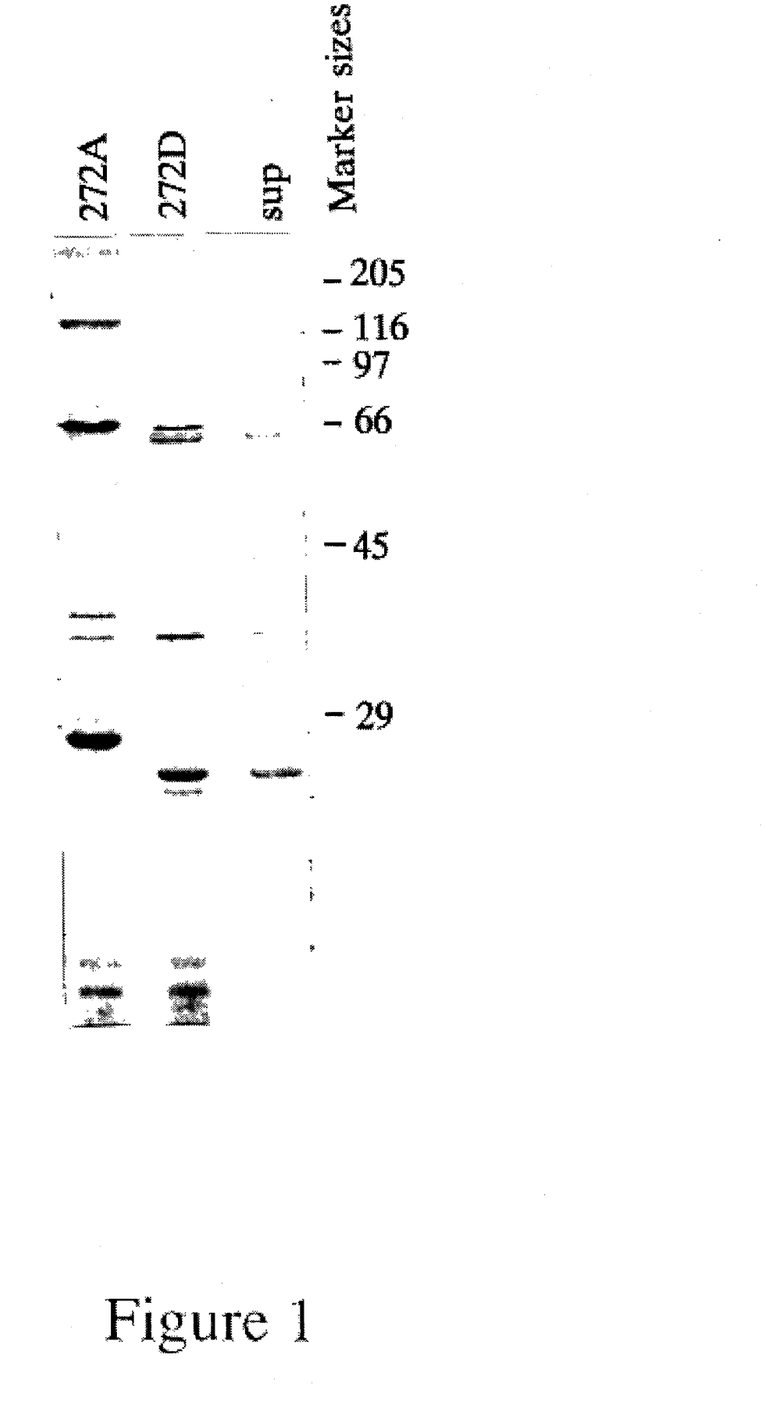
FIG. 1 shows SDS-PAGE analysis of protein profiles of B.t. cultures treated as described herein.

As shown by SDS-PAGE in FIG. 1, Treatment II results in a protein profile unaltered from the proteins produced as crystals in the PS123D1 culture (lane labeled 272A). We found that little, if any, of the crystal protein in Treatment II is soluble, and little proteolysis has taken place. The spore-crystal suspension subjected to Treatment I, however, displays an altered protein profile (lane labeled 272D). Most prominently, the bands of 133 and 127 kDa are missing and the band at 28 kDa is much reduced; prominent new bands of about 25, 23, and 21 kDa appear. Following centrifugation, most of the proteins observed in the suspension are found as soluble proteins in the supernatant, including those at 25 to 21 kDa (lane labeled sup). These aqueous suspensions were fed to the German cockroach, *Blatella germanica*, ad lib. The following results were obtained:

TABLE 3

| | Percent Mortality After Treatment | | |
|---|---|---|---|
| | Day 6 | Day 10 | Day 21 |
| Treatment I | 74 | 100 | 100 |
| Treatment II | 0 | 0 | 4 |
| Control | 0 | 0 | 2 |

EXAMPLE 4

Activated Toxins from *B.t.*i.

The removal of a portion of the N-terminus of the 123D1 28 kDa toxin was found to result in an advantageous activation of this toxin which increased the potency of its activity. The truncated toxin was found to have advantageous biological activity. Removal of amino acids can be accomplished by treatment with trypsin or other appropriate enzyme, or enzyme mixture, such as Pronase or endogenous proteins in *B.t.* culture broths. Other biologically active fragments could be obtained by those skilled in the art using the teachings provided herein.

As those skilled in the art having the benefit of this disclosure would readily recognize, the specific media used to grow the *B.t.* culture can be modified to achieve optimum activation of the *B.t.* toxin. For example, the cell density can be modulated by adjusting or changing the culture medium. Also, media having proteases therein can be used to enhance the activation of the *B.t.* toxins.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

U.S. Patents

U.S. Pat. No. 4,448,885.
U.S. Pat. No. 4,467,036.
U.S. Pat. No. 4,695,455
U.S. Pat. No. 4,695,462.
U.S. Pat. No. 4,797,276.
U.S. Pat. No. 4,849,217.
U.S. Pat. No. 4,853,331.
U.S. Pat. No. 4,918,006.
U.S. Pat. No. 4,948,734.
U.S. Pat. No. 5,135,867.
U.S. Pat. No. 5,151,363.

OTHER REFERENCES

Beegle, C. C., (1978) "Use of Entomogenous Bacteria in Agroecosystems," *Developments in Industrial Microbiology* 20:97–104.

Couch, T. L. (1980) "Mosquito Pathogenicity of Bacillus thuringiensis var. israelensis," *Developments in Industrial Microbiology* 22:61–76.

Feitelson, J. S., J. Payne, L. Kim [1992] *Bio/Technology* 10:271–275.

Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255.

Gaertner, F. H., L. Kim [1988] TIBTECH 6:S4–S7.

Höfte, H., H. R. Whiteley [1989] *Microbiological Reviews* 52(2):242–255.

Höfte, H. R., K. Annys, B. Lambert, S. Jansens, P. Soetaert, M. Peferoen (1992) "Novel *Bacillus thuringiensis* insecticidal crystal protein with a silent activity against coleopteran larvae," *Appl. Environ. Microbiol.* 58:2536–2542.

Humason, Gretchen L., *Animal Tissue Techniques*, W. H. Freeman and Company, 1967.

Jacquet, J., R. Hutter, P. Luthy (1987) "Specificity of *Bacillus thudngiensis* delta-endotoxin," *Appl. Environ. Microbiol.* 53:500–504.

Krieg, A., A. M. Huger, G. A. Langenbruch, W. Schnetter (1983) *Z. ang. Ent.* 96:500–508.

Pfannenstiel, M. A., E. J. Ross, V. C. Kramer, K. W. Nickerson [1984] *FEMS Microbiol. Lett.* 21:39.

Prefontaine, G., P. Fast, P. C. K. Lau, M. A. Hefford, Z. Hanna, R. Brosseau [1987] *Appl. Environ. Microbiol.* 53(12):2808–2814.

Reichenberg, D., in *Ion Exchangers in Organic and Biochemistry* (C. Calmon and T. R. E. Kressman, eds.), Interscience, New York, 1957.

Schnepf, H. E., H. R. Whiteley [1981] *Proc. Natl. Acad. Sci. USA* 78:2893–2897.

Singh, G. J. P., S. Gill (1985) "Myotoxic and Neurotoxic Activity of *Bacillus thudngiensis* var. israelensis Crystal Toxin," *Pesticide Biochemistry and Physiology* 24:406–414.

We claim:

1. A method for controlling cockroaches which comprises feeding said cockroaches an effective mount of a *Bacillus thuringiemsis* var. israelensis toxin of between about 25 kD and about 33 kD as measured by SDS PAGE.

2. The method, according to claim 1, wherein said toxin is truncated compared to the full length toxin as it is naturally expressed.

3. The method, according to claim 1, wherein said toxin is from *Bacillus thuringiensis* isolate PS123D1, having the activity against cockroaches characteristic of NRRL B-21011; or a mutant of said isolate which has activity against cockroaches.

4. The method, according to claim 1, wherein said cockroaches are selected from the group consisting of German cockroaches (*Blatella germanica*), Oriental cockroaches (*Blatta orientalis*), American cockroaches (*Pedplaneta*

*americana*) and Brown cockroaches (*Pedplaneta americana*).

5. The method, according to claim 1, wherein said cockroaches are German cockroaches (*Blatella germanica*).

6. The method, according to claim 1, which comprises growing in culture said *Bacillus thuringiensis* var. israelensis under conditions which facilitate the activation of said toxin by raising the pH of the culture.

7. The method, according to claim 6, wherein said activation is effected by the truncation of said *Bacillus thuringiensis* var. israelensis toxin.

8. The method, according to claim 1, which comprises adding a protease to a *Bacillus thuringiensis* var. israelensis culture, or a supernatant thereof.

9. A method for controlling cockroaches which comprises
   (1) preparing a bait comprising a Bacillus thuringiensis var. israelensis isolate; or spores, crystals, or toxins of said isolate; and
   (2) placing said bait in areas visited by cockroaches.

\* \* \* \* \*

UNITED STATES PATENT AND TRADEMARK OFFICE
CERTIFICATE OF CORRECTION

PATENT NO.    :    5,508,032

DATED         :    April 16, 1996

INVENTOR(S)   :    H. Ernest Schnepf, John B. Randall, Jewel M. Payne

It is certified that error appears in the above-identified patent and that said Letters Patent is hereby corrected as shown below:

Column 1: Line 26: "thudngiensis" should read --thuringiensis--; Line 32: "israelends and B.t. var. tenebdonis" should read --israelensis and B.t. var. tenebrionis--; Line 35: "Krieget al," should read --Krieg et al.,--; Line 42: "WhiteIcy" should read --Whiteley--; Line 44: "CryII" should read --CryII--; Line 51: "protoms" should read --protoxins--; Line 54: "WhiteIcy" should read --Whiteley--.

Column 2: Line 23: "altergins" should read --allergins--; Line 49: "routants." should read --mutants.--.

Column 3: Line 22: "thudngiensis" should read --thuringiensis--; Line 38: "toms" should read --toxins--.

Column 5: Line 24: "toms." should read --toxins.--.

Column 7: Line 16: "Metarhiziurn" should read --Metarhizium--; Line 20: "Agobacterium" should read --Agrobacterium--.

Column 8: Line 65: "to,tin." should read --toxin.--.

UNITED STATES PATENT AND TRADEMARK OFFICE
CERTIFICATE OF CORRECTION

PATENT NO. : 5,508,032

DATED : April 16, 1996

INVENTOR(S) : H. Ernest Schnepf, John B. Randall, Jewel M. Payne

It is certified that error appears in the above-identified patent and that said Letters Patent is hereby corrected as shown below:

Column 12: Line 33: "thudngiensis" should read --thuringiensis--; Line 48: "thudngiensis" should read --thuringiensis--; Line 53: "mount" should read --amount--; Line 54: "thuringiemsis" should read --thuringiensis--; Line 67: "(Pedplaneta" should read --(Periplaneta--.

Column 13: Line 1: "(Pedplaneta" should read --(Periplaneta--.

Signed and Sealed this

Twentieth Day of May, 1997

*Attest:*

BRUCE LEHMAN

*Attesting Officer*     *Commissioner of Patents and Trademarks*